BEGONIA PLANT
Filed July 16, 1975
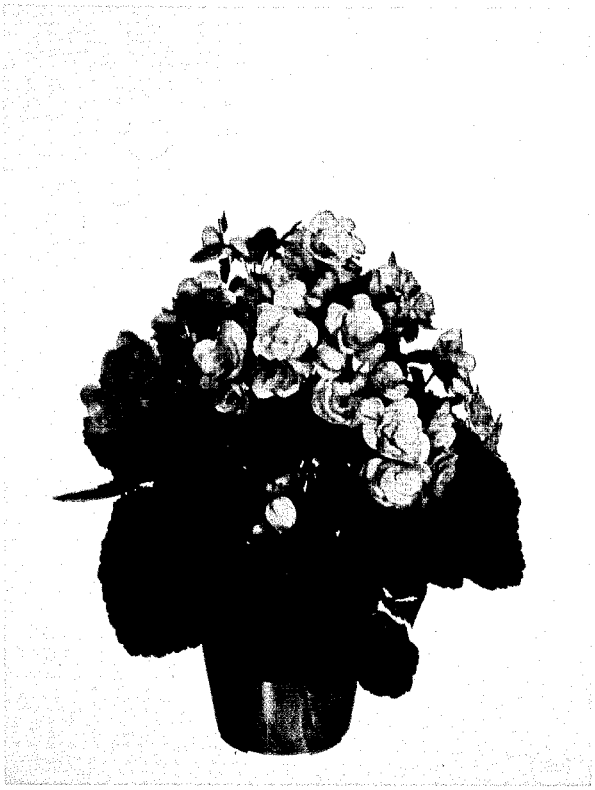

United States Patent

Plant Pat. 3,967

Patented Oct. 26, 1976

1

3,967

BEGONIA PLANT

Margarete Rohde-Rieger, Nurtingen, Germany, assignor to Mikkelsens, Inc., Ashtabula, Ohio Filed July 16, 1975, Ser. No. 596,453

Int. Cl.[2] A01H 5/00

U.S. Cl. Plt.—68

1 Claim

The present invention relates to a new and distinctive cultivar of begonia plant, botanically known as *begonia elatior* (*hiemalis*—Fotsch), and known by the cultivar name Nixe.

The new cultivar was discovered by me in a group of begonia seedlings from hybridized seed in a controlled breeding program. The seed parent is *Begonia tuberhybrida* (unnamed and unpatented) and the pollen parent is *Begonia socotrana* (unnamed and unpatented). Asexual reproduction by stem and leaf cuttings has reproduced the unique features of the new cultivar through successive propagations.

The following characteristics when combined distinguish the new begonia from other begonias commercially known and used in the floriculture industry:

1. Bright medium red, double flowers.
2. Short, full, compact, and upright growth.
3. A very high degree of self-branching, thereby resulting in the new cultivar being valuable for commercial pot plant production and for propagation by stem cuttings.
4. Round, heavily textured dark green foliage with nearly complete edges.
5. Leaf cuttings propagate 7 to 14 days more rapidly than the variety Schwabenland, disclosed in U.S. Letters Plant Patent 3,320, granted to Otto Rieger Mar. 13, 1973.
6. Leaf cuttings consistently produce four to six adventitious shoots at all times of the year whereas the Schwabenland types are inconsistent in the summer months.
7. Keeping quality of the flowers is better than in the Schwabenland types, but more importantly the flowering persists for four to six weeks longer.
8. Leaf area is very uniform on each plant and remains quite constant at maturity. Plant spacing can be decreased without jeopardizing quality.
9. Plant growth stays short and compact in all seasons so that growth retardants are not needed in summer months.

The accompanying colored photograph illustrates the overall appearance of the new cultivar and when grown under commercial practices in Nurtingen, Germany, and shows the colors as true as it is reasonably possible to obtain in a colored reproduction of this type.

The following is a detailed description of my new begonia variety based on plants produced under commercial practices in Nurtingen, Germany. Color references are made to the Royal Horticultural Society Colour Chart except where general color terms of ordinary dictionary significance are used.

*Parentage:* The new cultivar is the result of controlled pollination of a selected *Begonia tuberhybrida* or the seed parent crossed with *Begonia socotrana* as the pollen parent.

*Propagation:* Leaf cuttings produced a saleable young plant with consistently four or more shoots in 7–14 less days than Schwabenland, disclosed in U.S. Letters Plant Patent 3,320, granted Mar. 13, 1973 to Otto Rieger, deceased. Profuse self branching also allows the new cultivar to be propagated by stem cuttings in four weeks.

2

*Rooting Habit:* Either leaf cuttings or stem cutting will develop fine dendritic roots in four weeks. However, the roots are fine and sensitive and not particularly strong. Loose and mild soil is therefore necessary.

*Plant Form:* Upright and compact.

*Habit of Growth:* Medium rate of growth for this class of begonia, producing an upright, self-branching, close internoded, compact plant.

*Blooming Habit:* Very profuse flowering over an extended period of time.

*Blooming Season:* Natural blooming season is in November but with controlled environmental conditions of temperature and daylight this variety can be brought into flower anytime of the year.

*Foliage:* Quite dense, roundish and uniform in size and shape at maturity.

(a) *Size:* Approximately 10 cm across by 8 cm long.
(b) *Shape:* Nearly circular with very little sinus indentation.
(c) *Texture:* Leathery.
(d) *Margin:* Very fine serration.
(e) *Color:* Young: top—yellow green 147A; underside—red-purple 60A. Mature: top—darker than 139A; underside—green, heavily infused with red-purple 60A.

*Disease Resistance:* Resistance to powdery mildew is about the same as in Schwabenland when plants are grown under conditions favorable to that disease.

FLOWERS

*Borne*—On strong upright peduncles with two or three originating at the same point on the main flowering stem. This feature tends to give the appearance of several flowers clustered together in the floral display.

*Quantity*—Flowers in bloom at one time is somewhat above average for elatior type begonias.

*Flower Buds*—Flat, measuring approximately 2 cm in diameter before opening.

*Tepals*—Number between 14 to 18, measuring 25 mm wide by 30 mm long. Total flower size is 5 to 6 cm in diameter.

*Tepal Color*—Topside starts at red 45B turning to light red 50B at maturity. Underside 45D to 50B.

I claim:

1. A new and distinct cultivar of begonia plant characterized particularly by its bright medium red, double flowers; short, full compact and upright growth habit in all seasons; a high degrese of self-branching; round, heavily textured dark green foliage with nearly complete edges; rapid propagation from leaf cuttings, with the cuttings consistently producing four to six adventitious shoots at all times of the year; excellent keeping quality and long flowering period and by its uniform leaf area on each plant.

No references cited.

ROBERT E. BAGWILL, Primary Examiner